United States Patent [19]

Quirk et al.

[11] Patent Number: 4,658,050

[45] Date of Patent: Apr. 14, 1987

[54] NOVEL PROCESS FOR THE PREPARATION OF HALOPROPYLTRIALKOXYSILANES AND HALOPROPYLALKYLALKOXYSILANES

[75] Inventors: Jennifer M. Quirk, Highland, Md.; Bernard Kanner, West Nyack, N.Y.

[73] Assignee: Union Carbide Corporation, Danbury, Conn.

[21] Appl. No.: 846,176

[22] Filed: Mar. 31, 1986

[51] Int. Cl.$^4$ ............................ C07F 7/08; C07F 7/18
[52] U.S. Cl. .................................................... 556/479
[58] Field of Search ......................................... 556/479

[56] References Cited

U.S. PATENT DOCUMENTS

| | | | |
|---|---|---|---|
| 2,823,218 | 2/1968 | Speier et al. | 556/479 X |
| 3,658,866 | 4/1972 | Tsuji et al. | 556/479 |
| 3,714,212 | 1/1973 | Lengnick | 556/479 |
| 3,907,852 | 9/1975 | Oswald et al. | 556/479 X |
| 4,578,496 | 3/1986 | Panster et al. | 556/479 |
| 4,584,395 | 4/1986 | Panster et al. | 556/479 |

Primary Examiner—Paul F. Shaver
Attorney, Agent, or Firm—Steven H. Flynn

[57] ABSTRACT

A process for the preparation of halopropyltrialkoxysilanes and halopropylalkylalkoxysilanes comprising the hydrosilation of allyl halides (including substituted allyl halides) with trialkoxysilanes and alkylalkoxy silanes over specific iridium-containing catalysts.

15 Claims, No Drawings

NOVEL PROCESS FOR THE PREPARATION OF HALOPROPYLTRIALKOXYSILANES AND HALOPROPYLALKYLALKOXYSILANES

FIELD OF THE INVENTION

This invention relates to a novel process for preparing halopropyltrialkoxysilanes and halopropylalkylalkoxysilanes. More particularly, this invention relates to a process for hydrosilation of allyl halides with trialkoxysilanes and alkylalkoxysilanes, in the presence of specific iridium containing catalysts.

BACKGROUND OF THE INVENTION

The hydrosilation of allyl chloride and related compounds have previously been catalyzed by platinum- or rhodium- containing compounds. For instance, the use of platinum containing hydrosilation catalysts is disclosed in U.S. Pat. Nos. 2,823,218, 3,814,730, 3,715,334, 3,516,946, 3,474,123, 3,419,593, 3,220,972, 3,188,299, 3,178,464, 3,159,601, German Patent No. 1,165,028 and published U.K. Patent Application No. 2,019,426A. Hydrosilation over chloro-rhodium compounds has been disclosed in U.S. Pat. Nos. 3,296,291 and 3,564,266. However, the yields obtained through the use of these catalysts are typically low, i.e., 40 to 70 percent. It is believed that these low yields are attributable to the existence of competing reduction reactions. For example, the addition of trichlorosilane to allyl chloride over a platinum catalyst results in the following two reaction pathways:

$CH_2 = CHCH_2Cl +$

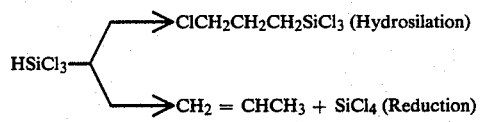

It has been reported in Zhurnal Obshchei Khimii, Vol. 44, No. 11 pp. 2439–2442 that the rate of the above reduction reaction increases appreciably as the halogen atoms of the silane are replaced with organic moieties presumably due to steric factors. For example, the reaction of trimethoxysilane with allyl chloride over a chloroplatinic acid catalyst produces 3-chloro-propyltrimethoxysilane in yields of less than 40%. Major by-products generated through the reduction reaction are trimethoxychlorosilane and propylene. The increased rate of the competing reduction reaction is thought to be responsible for lower yields of the desired hydrosilation product.

Accordingly, the development of a hydrosilation process which effectively generates halopropylalkoxysilanes and halopropylalkylalkoxysilanes from alkoxysilanes and alkylalkoxysilanes, respectively, in yields above those realized through the use of the processes of the prior art is highly desirable. Applicants have met this goal through the development of the instant process which is capable of producing yields in excess of 75 percent. These improved product yields realized through the instant process are further quite unexpected in view of the literature which discloses that iridium-containing catalysts are ineffective in the hydrosilyation of 1-olefins, (see, for example *Iridium Complexes as Hydrosilyation Catalysts*, Journal of Molecular Catalysis, 29 (1985) p. 60.)

SUMMARY OF THE INVENTION

This invention involves a novel process for the preparation of halopropyltrialkoxysilanes and halopropylalkylalkoxysilanes having the formula

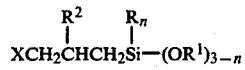

wherein R and $R^1$ individually are alkyl groups having from 1 to 10 carbon atoms; $R^2$ is hydrogen or an alkyl group having from 1 to 6 carbon atoms, X is chlorine, bromine or iodine, and n has a value of 0, 1 or 2, which process comprises reacting a silane of the formula

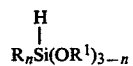

wherein R, $R^1$, and n are as defined above, with a compound of the formula

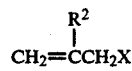

wherein $R^2$ and X are as defined above, in the presence of a catalytic amount of an iridium containing dimer complex of the formula $[Ir(Q)L]_2$ wherein Q is selected from the group consisting of 1,3-butadiene, 1,3-hexadiene, 1,3-cyclohexadiene, 1,3-cyclooctadiene, 1,5-cyclooctadiene and norbornadiene and L is chlorine, bromine or iodine.

Silanes useful in the instant process are those of the formula

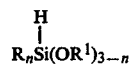

wherein R and $R^1$ are each alkyl groups having from 1 to about 10 carbon atoms and n is 0, 1 or 2. Preferred silane materials useful in the process of this invention include those wherein n is 0 and R and $R^1$ are methyl, ethyl, propyl, isopropyl or butyl groups. Illustrative of the silanes that can be used in the process of this invention are triethoxysilane, trimethoxysilane, tripropoxysilane, tri-isopropoxysilane, tributoxysilane, methyldimethoxysilane, ethyldimethoxysilane, methyldiethoxysilane, dimethylmethoxysilane, trioctyloxysilane, methyldioctyloxysilane, and dimethyloctyloxysilane.

Allyl halides and their derivatives useful in the process of this invention are those of the formula

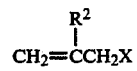

wherein $R^2$ is hydrogen or an alkyl group having from one to about six carbon atoms and X is chlorine, bromine or iodine. Preferred are allyl chloride and methallyl chloride. Most preferred due to ecomonic considerations is allyl chloride.

The weight ratio of the silane starting material to allyl halides useful in the process of this invention can range from 5:1 to 1:5 and is preferably in the range of 1.5:1 to 1:1.5. Most preferably, the ratio of silane to allyl halide is about 1:1.

The iridium catalysts useful in the process of the claimed invention comprise iridium diene halide complex dimers of the formula $$[Ir(Q)L]_2$$

wherein Q is selected from the group consisting of 1,3-butadiene, 1,3-hexadiene, 1,3-cyclohexadiene, 1,3-cyclooctadiene and 1,5-cyclooctadiene and norbornadiene and L is chlorine, bromine or iodine. Preferred catalytic compositions are those wherein L is as stated above and Q is 1,5-cyclooctadiene. Most preferred is the catalytic composition wherein L is chlorine and Q is 1,5-cyclooctadiene.

The preparation of the catalysts utilized in the process of this invention is well documented in the literature. For example, the preparation of [Ir(cyclooctadiene)Cl]$_2$ is disclosed in Z. Naturforsch., Teil B., 20, (1965) at page 602 and Chem. Ber., 99 (1966) at page 3610. Both these preparations involve the reduction of iridium (IV) salts, such as Na$_2$IrCl$_6$ with 1,5-cyclooctadiene in the presence of aqueous ethanol.

The production of [Ir(1,5-cyclooctadiene)]$_2$ through the reaction of H$_2$IrCl$_6$.6H$_2$O and 1,3-cyclooctadiene is further disclosed in Chem. Ber., 99 (1966) at page 3610. The Journal of Organometallurgical Chemistry, vol. 92 (1975) at page 107 discloses production of this material through the reaction of Na$_2$IrCl$_6$ and 1,4-cyclooctadiene.

The Journal of Organomet. Chem., vol. 135 (1977) at page 395 discloses the production of [HClIr(1,5-cyclooctadiene)Cl$_2$]$_2$ through reaction of H$_2$IrCl$_6$ with 1,5-cyclooctadiene in iso-propanol. The product of this reaction is then be dehydrohalogenated with aqueous sodium acetate to produce [Ir(1,5-cyclooctadiene)Cl]$_2$.

Formation of the iodo-complex [Ir(1,5-cyclooctadiene)I]$_2$ as disclosed in Chemical Abstracts, vol. 85 96591X (1976) involves the reaction of IrI$_3$.3H$_2$O and 1,5-cyclooctadiene in aqueous ethanol.

Catalytic complexes other than that which contains 1,5-cyclooctadiene may be prepared by a simple displacement reaction with the [Ir(2,5-cyclooctadiene)]$_2$ material, and an excess of the desired diene. The catalyst so-produced may then be recovered as a solid.

The concentration of the iridium-containing catalyst complexes used in the process of this invention depends on reaction temperature and time but, in general, should be greater than about 5 ppm iridium, based on the total combined weight of the silane and allyl halide used. The upper limit on the catalyst concentration is not critical and would be determined largely by catalyst solubility and economic considerations. Preferably, the catalyst concentration should be greater than about 40 ppm iridium, and most preferably in the range of about 50–900 ppm iridium, based on the total combined weight of the silane and allyl halide.

The hydrosilation reaction involved in the process of this invention can be conducted at a temperature of from about 20° C. to 200° C., preferably between about 50° C. to about 150° C. and most preferably between about 60° C. to about 125° C. The pressure of the reaction is not critical. The reaction can be conducted at atmospheric, sub atmospheric or super-atmospheric pressure. It is preferable to carry out the claimed process at about atmospheric pressure.

The reaction time used in the process of this invention will vary depending upon the other conditions, such as amount of catalyst or the reaction temperature. The higher the catalyst concentration and reaction temperature, the shorter the reaction time. In general, when the catalyst concentration is in the range of 50–900 ppm iridium based on the total combined weight of the silane and allyl halide used and the reaction temperature is between about 60° C. to about 125° C., a reaction time of about 2–3 hours is generally sufficient although the yield of the reaction is not significantly affected when a longer reaction time is used.

Solvent is generally not necessary for the hydrosilation reaction involved in the process of this invention. However, the use of solvent may be desired to increase catalyst solubility in the reaction mixture. If a solvent is employed, those useful in the claimed process are those which do not adversely react with the reactants, catalyst or reaction products. Suitable solvents include xylene, toluene and tri-isopropylbenzene.

The halopropyltrialkoxysilanes and haloproplyalkylalkoxysilanes obtained by the process of this invention are useful, for example, as intermediates in the production of organo-functional silane coupling agents. The conversion of the products of the instant invention to said coupling agents is well known in the art as shown, for example, in the *Chemistry and Technology of Silicones* by Walter Nole (Academy Press, 1968) pages 147, 148 and 158. The conversion basically comprises replacement of the halogen moiety with, for example, hydroxyl, amino or mercapto groups.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present as limitations on the present invention except as set forth in the appended claims. All parts and percentages are by weight unless otherwise specified.

EXAMPLE 1

Into a 3 cc "Swagelok" capped stainless steel tube were added triethoxysilane (1.0 gram, 0.006 mole), allyl chloride (0.5 grams, 0.006 mole), and xylene (0.5 grams). Also introduced therein was 100 ppm (0.19 mg) of [Ir(1,5 cyclooctadiene)Cl]$_2$.

The reaction mixture was then heated to 80° C. in a fluidized sand bath. This temperature was maintained for four (4) hours, after which the reaction mixture was cooled to room temperature.

Analysis of the reaction products determined that 3-chloropropyltriethoxysilane was produced in yields slightly greater than 75%

EXAMPLE 2

The procedure set forth in Example 1 was followed except that a reaction mixture consisting of methyldiethoxysilane (5.0 gram, 0.047 mole), allyl chloride (3.6 grams, 0.047 mole), xylene (0.4 grams) and 0.95 grams of catalyst (100 ppm) was introduced into a 45 cc Parr bomb.

Analysis of the reaction products determined that 3-chloropropylmethyldiethoxysilane was produced in yields of about 70%.

EXAMPLE 3

The procedure set forth in Example 1 was followed except that the reaction mixture consisted of methyldiethoxysilane (1.0 gram, 0.007 mole), allyl chloride (0.6 grams, 0.007 mole), xylene (0.4 grams) and 0.21 grams of catalyst (100 ppm).

Analysis of the reaction products determined that 3-chloropropylmethyldiethoxysilane was produced in yields slightly greater than 75%.

EXAMPLE 4

The procedure set forth in Example 1 was followed except that the reaction mixture consisted of trimethoxysilane (1.0 grams, 0.008 mole), allyl chloride (0.6 grams, 0.006 mole), xylene (0.4 grams) and 0.18 mg of catalyst. (100 ppm).

Analysis of the product mixture determined that the yield of 3-chloropropyltrimethoxysilane exceeded 75%.

EXAMPLE 5

Into a 45 cc Parr bomb was introduced a reaction mixture consisted of triisopropoxysilane (5.0 grams, 0.024 mole), allyl chloride (1.9 grams, 0.024 mole), xylene (2.0 grams) and 1.91 grams of catalyst. (200 ppm).

The reaction mixture was then heated to 150° C. in a fluidized sand bed. This temperature was maintained for six (6) hours, after which the reaction mixture was cooled to room temperature.

Analysis of the reaction products determined that chloropropyltriisopropoxysilane was produced in yields exceeding 70%.

EXAMPLE 6

The procedure set forth in Example 1 was followed except the reaction temperature was increased from 80° C. to 100° C. The reaction time was maintained at four (4) hours.

Analysis of the reaction products obtained that 3-chloropropyltriethoxysilane was produced in yields exceeding 70%.

EXAMPLE 7

The procedure set forth in Example 1 was followed except that the reaction temperature was increased from 80° C. to 135° C. Reaction time was maintained at four (4) hours.

Analysis of the reaction products determined that 3-chloropropyltriethoxysilane was produced in yields of approximately 75%.

COMPARATIVE EXAMPLE 1

The procedure set forth in Example 1 was followed except that 1) $H_2PtCl_6$ (100 ppm) was used as the catalyst and 2) the reaction temperature was increased to 100° C.

Analysis of the reaction products determined that the yield of 3-chloropropyltriethoxysilane was less than 10%, while the major components of the product mixture consisted of chlorotriethoxysilane and tetraethoxysilane.

COMPARATIVE EXAMPLE 2

The procedure set forth in Example 1 was followed except that 1) the catalyst employed was $PtCl_2(PPh_3)_2$ and 2) the reaction temperature was increased to 150° C.

Analysis of the product mixture revealed that no 3-chloropropyltriethoxysilane was produced. However, tetraethoxysilane, chlorotriethoxysilane as well as unreacted triethoxysilane and allyl chloride were found to be present.

COMPARATIVE EXAMPLE 3

The procedure set forth in Example 2 was followed except that 1) the catalyst employed was $[Rh(1,5\text{-cyclooctadiene})Cl]_2$ and the reaction temperature was increased to 135° C.

Analysis of the product mixture revealed that no 3-chloropropyltriethoxysilane was produced. The major products of the reaction mixture were found to be tetraethoxysilane and chlorotriethoxysilane.

What is claimed is:

1. A process for the preparation of a compound of the formula

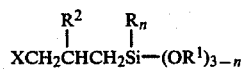

wherein R and $R^1$ individually are alkyl groups having from 1 to 6 carbon atoms; $R^2$ is hydrogen, or an alkyl group having from 1 to 6 carbon atoms; X is chlorine, bromine or iodine and n has a value of 0, 1 or 2, which process comprises reacting a silane having the formula

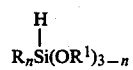

wherein R, $R^1$ and n are as defined above with a compound having the formula

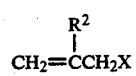

wherein $R^2$ and X are as defined above in the presence of a catalytic amount of an iridium containing dimer complex of the formula

wherein Q is selected from the group consisting of 1,3-butadiene, 1,3-hexadiene, 1,3-cyclohexadiene, 1,3-cyclooctadiene, 1,5-cyclooctadiene and norbornadiene and L is chlorine, bromine or iodine.

2. The process of claim 1 wherein R is selected from the group consisting of methyl, ethyl, propyl, isopropyl and butyl.

3. The process of claim 1 wherein $R^1$ is selected from the group consisting of methyl, ethyl, propyl, isopropyl and butyl.

4. The process of claim 1 wherein R is ethyl, n equals 0, X is Cl and $R^2$ is H.

5. The process of claim 1 wherein R is methyl, $R^1$ is methyl, n equals 1, X is Cl and $R^2$ is H.

6. The process of claim 1 wherein R is methyl, $R^1$ is ethyl, n equals 1, X is Cl and $R^2$ is H.

7. The process of claim 1 wherein $R^1$ is methyl, n equals 0, X is Cl and $R^2$ is H.

8. The process of claim 1 wherein $R^1$ is iso-propyl, n equals 0, X is Cl and $R^2$ is H.

9. The process of claim 1 wherein Q is 1,5-cyclooctadiene and L is Cl.

10. The process of claim 1 wherein said reaction is conducted at a temperature of from about 20° C. to about 200° C.

11. The process of claim 10 wherein the temperature is from abut 50° C. to about 150° C.

12. The process of claim 10 wherein the temperature is from about 60° C. to about 125° C.

13. The process of claim 1 wherein the iridium-containing dimer complex is present in amounts such that at least about 40 ppm of iridium is present based upon the combined weight of the silane and the allyl halide.

14. A process for the preparation of a compound of the formula

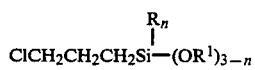

$$ClCH_2CH_2CH_2Si{-}(OR^1)_{3-n}$$ with $R_n$ above Si wherein R and $R^1$ are individually methyl, ethyl or iso-propyl, and n is 0 or 1 which comprises reacting at a temperature of from about 20° C. to about 200° C.:
 a silane having the formula

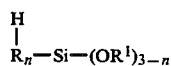

$$R_n{-}Si{-}(OR^1)_{3-n}$$ with H above Si wherein R, $R^1$ and n are as defined above, with a compound of the formula

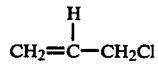

$$CH_2{=}C{-}CH_2Cl$$ with H above C in the presence of a catalytic amount of

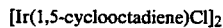

[Ir(1,5-cyclooctadiene)Cl]$_2$

15. The process of claim 14 wherein said catalytic amount of [Ir(1,5-cyclooctadiene)Cl]$_2$ is such that from about 40 to about than 900 ppm of iridium is present based upon the combined weight of the silane and allyl halide.

* * * * *